United States Patent
Wen et al.

(10) Patent No.: US 10,751,458 B2
(45) Date of Patent: Aug. 25, 2020

(54) DISPLACEMENT SENSING DEVICE AND PERITONEAL DIALYSIS SYSTEM

(71) Applicants: Acer Incorporated, New Taipei (TW); BENEPET CO., LTD., Taipei (TW)

(72) Inventors: Chun-Hung Wen, New Taipei (TW); Wei-Chen Lai, New Taipei (TW); Pu-De Ciou, New Taipei (TW); Wen-Pin Chang, New Taipei (TW); Tsung-Hsun Wu, New Taipei (TW); Wen-Shu Lee, New Taipei (TW); Ta-Lun Tan, Taipei (TW)

(73) Assignees: Acer Incorporated, New Taipei (TW); BENEPET CO., LTD., Taipei (TW)

( * ) Notice: Subject to any disclaimer, the term of this patent is extended or adjusted under 35 U.S.C. 154(b) by 301 days.

(21) Appl. No.: 15/871,014

(22) Filed: Jan. 14, 2018

(65) Prior Publication Data

US 2018/0333527 A1 Nov. 22, 2018

(30) Foreign Application Priority Data

May 19, 2017 (TW) .............................. 106207198 U

(51) Int. Cl.
*A61M 1/28* (2006.01)
*A61M 1/10* (2006.01)
(Continued)

(52) U.S. Cl.
CPC .......... *A61M 1/282* (2014.02); *A61M 1/1037* (2013.01); *A61M 1/28* (2013.01);
(Continued)

(58) Field of Classification Search
CPC ................ A61M 1/282; A61M 5/1684; A61M 5/14216; A61M 5/31573; A61M 1/28; A61M 1/1037; A61M 2205/3389; A61M 2205/3306; A61M 5/1452; A61M 2005/31588; A61M 2205/3327; A61M 2205/3334; F04B 13/00; F04B 17/03; F04B 2201/0201; F04B 43/06; F04B 43/12

See application file for complete search history.

(56) References Cited

U.S. PATENT DOCUMENTS

| 4,838,857 A | 6/1989 | Strowe et al. |
| 2014/0188076 A1* | 7/2014 | Kamen ............... A61M 5/1458 604/506 |

FOREIGN PATENT DOCUMENTS

| CN | 2248070 | 2/1997 |
| CN | 201348846 | 11/2009 |

(Continued)

*Primary Examiner* — Lauren P Farrar
(74) *Attorney, Agent, or Firm* — JCIPRNET

(57) ABSTRACT

A displacement sensing device is configured for a peritoneal dialysis system. The peritoneal dialysis system includes a housing and a syringe. The syringe is disposed on the housing and has a push rod. The displacement sensing device includes a guide rod, a probing module, and a resistance scale. The guide rod is coupled to the push rod, and the probing module is disposed in the housing and is fixed at the guide rod. The resistance scale is disposed at a side of the probing module. The probing module is configured to contact the resistance scale to obtain a resistance value of the resistance scale and determine a displacement magnitude of the push rod. In addition, a peritoneal dialysis system is also mentioned.

9 Claims, 4 Drawing Sheets

(51) Int. Cl.
  *F04B 13/00* (2006.01)
  *A61M 5/315* (2006.01)
  *F04B 17/03* (2006.01)
  *A61M 5/168* (2006.01)
  *A61M 5/142* (2006.01)
  *F04B 43/12* (2006.01)
  *F04B 43/06* (2006.01)
  *A61M 5/145* (2006.01)

(52) U.S. Cl.
  CPC ...... *A61M 5/14216* (2013.01); *A61M 5/1684* (2013.01); *A61M 5/31573* (2013.01); *F04B 13/00* (2013.01); *F04B 17/03* (2013.01); *A61M 5/1452* (2013.01); *A61M 2005/31588* (2013.01); *A61M 2205/3306* (2013.01); *A61M 2205/3327* (2013.01); *A61M 2205/3334* (2013.01); *A61M 2205/3389* (2013.01); *F04B 43/06* (2013.01); *F04B 43/12* (2013.01); *F04B 2201/0201* (2013.01)

(56) References Cited

FOREIGN PATENT DOCUMENTS

| | | |
|---|---|---|
| CN | 202096545 | 1/2012 |
| CN | 203534530 | 4/2014 |
| CN | 203874222 | 10/2014 |
| CN | 105392511 | 3/2016 |
| CN | 105466374 | 4/2016 |
| CN | 206120833 | 4/2017 |
| TW | 200627107 | 8/2006 |

\* cited by examiner

DISPLACEMENT SENSING DEVICE AND PERITONEAL DIALYSIS SYSTEM

CROSS-REFERENCE TO RELATED APPLICATION

This application claims the priority benefit of Taiwan application serial no. 106207198, filed on May 19, 2017. The entirety of the above-mentioned patent application is hereby incorporated by reference herein and made a part of this specification.

BACKGROUND

Technical Field

The disclosure relates to a displacement sensing device, and in particular, to a displacement sensing device for a peritoneal dialysis system.

Description of Related Art

With the development of medical technology and the advent of the aging society, the need for peritoneal dialysis systems and the like is rising. However, currently, in the internal structure of a general peritoneal dialysis system, a direct current motor works with a screw rod structure, for example, to push and pull a syringe, and a light blocking sensor works with a blocking bar to provide feedback to control a displacement distance of a push rod of the syringe. Together they form a motor control module.

However, a blocking bar is generally locked and attached by only two screws and thus has issues of assembly tolerance and deformation. Moreover, after long-time use, the blocking bar, which is made of a metal piece, for example, will have various issues such as corrosion, such that the light blocking sensor cannot be precisely controlled and aligned, so erroneous determination on the displacement distance of the push rod of the syringe may easily occur, and the amount of the injection dosage of the syringe cannot be precisely controlled. Therefore, during the treatment, the injection dosage may be excessively or insufficiently injected. Accordingly, how to effectively measure an actuation travel of the push rod of the syringe to further effectively control the injection amount of the syringe has become one of the issues to be solved in the art.

SUMMARY

The disclosure provides a displacement sensing device capable of more precisely sensing a displacement magnitude of a push rod of a syringe.

The disclosure provides a peritoneal dialysis system capable of more precisely controlling an injection amount of dosage of its syringe.

The displacement sensing device of the disclosure is configured for a peritoneal dialysis system. The peritoneal dialysis system includes a housing and a syringe. The syringe is disposed on the housing and has a push rod. The displacement sensing device includes a guide rod, a probing module, and a resistance scale. The guide rod is coupled to the push rod, and the probing module is disposed in the housing and is fixed at the guide rod. The resistance scale is disposed at a side of the probing module. The probing module is configured to contact the resistance scale to obtain a resistance value of the resistance scale and determine a displacement magnitude of the push rod.

The peritoneal dialysis system of the disclosure includes a housing, a syringe, and a displacement sensing device. The syringe is disposed on the housing, and the syringe has a push rod. The displacement sensing device is disposed in the housing. The displacement sensing device includes a guide rod, a probing module, and a resistance scale. The guide rod is coupled to the push rod, and the probing module is disposed in the housing and is fixed at the guide rod. The resistance scale is disposed at a side of the probing module. The probing module is configured to contact the resistance scale to obtain a resistance value of the resistance scale and determine a displacement magnitude of the push rod.

In an embodiment of the disclosure, the displacement sensing device further includes a driving element. The driving element is coupled to the guide rod and the push rod to drive the guide rod and the push rod to move.

In an embodiment of the disclosure, the driving element includes a stepping motor.

In an embodiment of the disclosure, the displacement sensing device further includes a sliding rod. The sliding rod is connected to the housing, and the sliding rod penetrates through the probing module. The probing module is configured to slide relatively to the sliding rod.

In an embodiment of the disclosure, the displacement sensing device further includes an optical sensor. The optical sensor is disposed at an actuating initial position of the probing module to perform return-to-zero calibration for traveling displacement of the probing module.

In an embodiment of the disclosure, the probing module includes an extension part, and the extension part includes an optical shutter corresponding to the optical sensor.

In an embodiment of the disclosure, the probing module further includes a threaded hole and a probe, and the probe is locked by screwed into the threaded hole to contact the resistance scale.

In an embodiment of the disclosure, the peritoneal dialysis system further includes a display element. The display element is disposed at a side of the housing to display a sensing result of the displacement sensing device.

In an embodiment of the disclosure, the peritoneal dialysis system further includes a fixing element. The fixing element is disposed between the guide rod and the push rod, and the guide rod and the push rod respectively penetrate through the fixing element along the same direction.

In light of the above, in the embodiments of the disclosure, the peritoneal dialysis system includes the displacement sensing device that senses the displacement magnitude of the push rod of the syringe to determine the amount drew and injected by the syringe. The displacement sensing device of the embodiments of the disclosure includes the probing module and the resistance scale. The probing module moves along with the guide rod and contacts the resistance scale to further obtain the resistance value at different positions of the resistance scale. The probing module determines the displacement magnitude of the push rod of the syringe according to the measured resistance value to further determine the amount drew or injected by the syringe. In the embodiments of the disclosure, through the resistance scale, the displacement sensing device can sense the displacement magnitude of the push rod of the syringe more precisely, and the amount of injection of the syringe can be more precisely controlled.

To provide a further understanding of the aforementioned and other features and advantages of the disclosure, exemplary embodiments, together with the reference drawings, are described in detail below.

DESCRIPTION OF THE EMBODIMENTS

Figure 1:
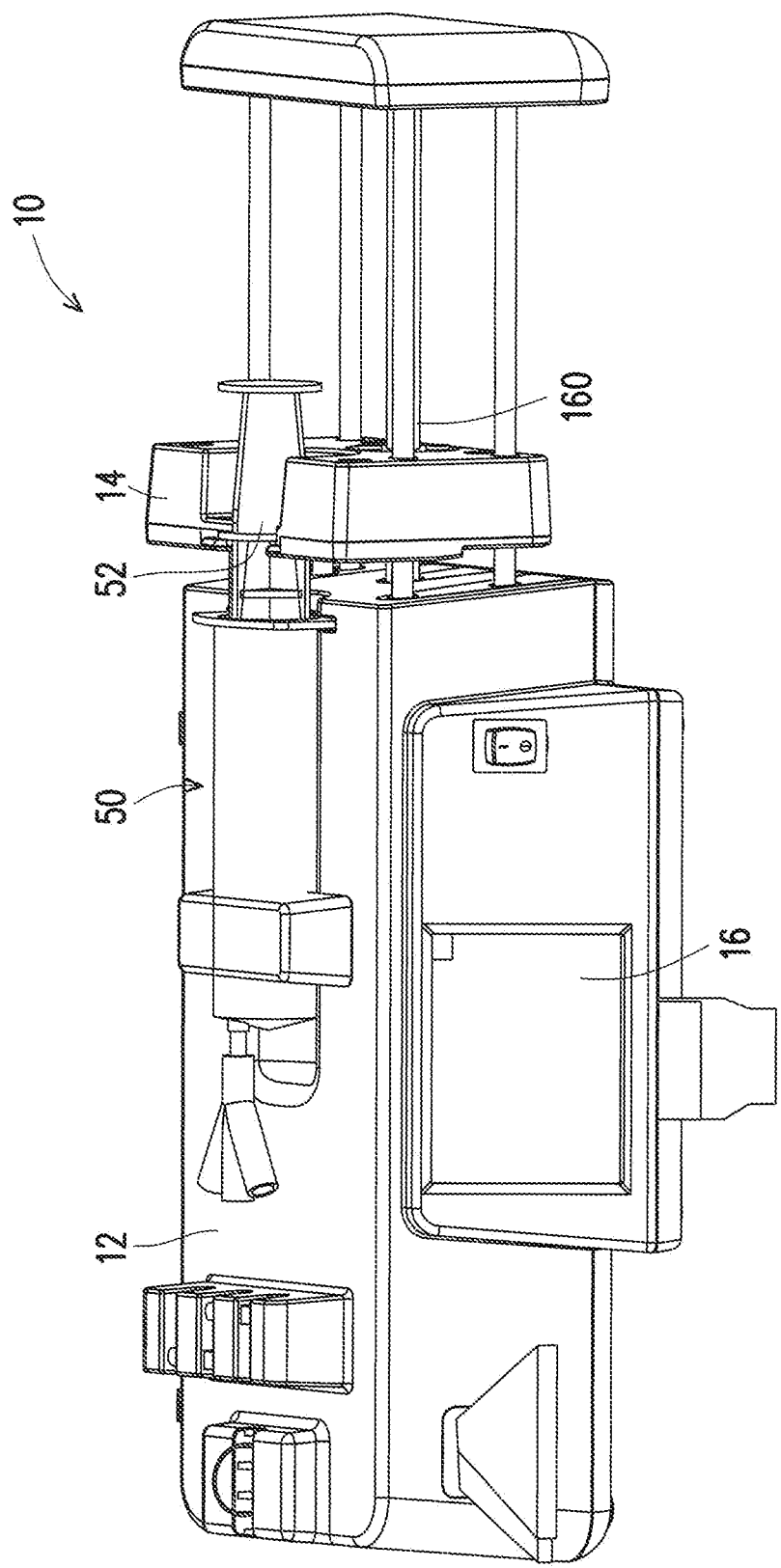
FIG. 1 is a schematic diagram illustrating a peritoneal dialysis system according to an embodiment of the disclosure.
Figure 2:
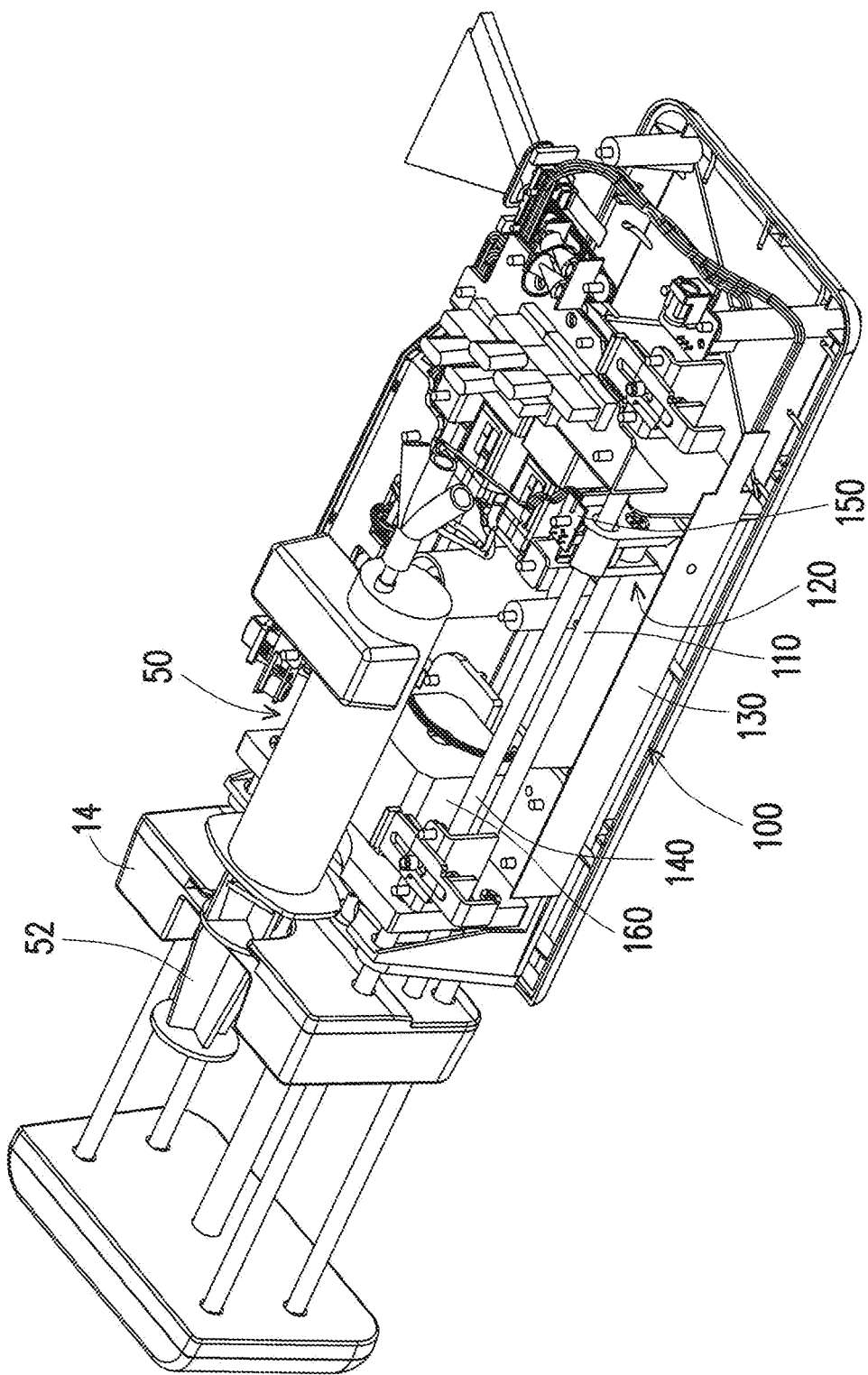
FIG. 2 is a schematic diagram illustrating a displacement sensing device of the peritoneal dialysis system of FIG. 1.

FIG. 1 is a schematic diagram illustrating a peritoneal dialysis system according to an embodiment of the disclosure. FIG. 2 is a schematic diagram illustrating a displacement sensing device of the peritoneal dialysis system of FIG. 1. Referring to FIG. 1 and FIG. 2, a peritoneal dialysis system 10 includes a housing 12, a syringe 50, and a displacement sensing device 100. The syringe 50 is disposed on the housing 12, and the syringe 50 has a push rod 52. In the present embodiment, the syringe 50 first takes in a liquid agent (e.g. medicament) to be injected, and then the syringe 50 injects the agent to be injected into a human body or an animal body.

As shown in FIG. 2, the displacement sensing device 100 is disposed in the housing 10, and the displacement sensing device 100 includes a guide rod 110, a probing module 120, and a resistance scale 130. The guide rod 110 is coupled to the push rod 52 of the syringe 50, the probing module 120 is fixed at the guide rod 110, and the resistance scale 130 is disposed at a side of the probing module 120. In the present embodiment, the guide rod 110 is configured to drive the probing module 120 and the push rod 52 to move towards the same direction. For example, when the push rod 52 is pulled out from inside of the syringe 50, the probing module 120 may also be moved towards a direction in which the push rod 52 is pushed out.

In the present embodiment, an extension direction of the resistance scale 130 is parallel to a moving direction of the probing module 120, and different positions on the resistance scale 130 may indicate different resistance values. The probing module 120 is configured to contact the resistance scale 130 to measure the resistance value at the position contacted by the probing module 120. In the present embodiment, the probing module 120 determines a displacement distance thereof (namely, the distance from where the probing module 120 is located to its actuating initial position) according to the measured resistance value to thereby obtain a displacement magnitude of the push rod 52 of the syringe 50.

In the present embodiment, the displacement sensing device 100 further includes a driving element 160, and the driving element 160 is, for example, a stepping motor. The driving element 160 is coupled to the guide rod 110 and the push rod 52 of the syringe 50, and the driving element 160 drives the guide rod 110 and the push rod 52 to move together along the same direction. Moreover, the driving element 160 compares the displacement magnitude of the guide rod 110 and the push rod 52 measured by the probing module 120 with a predetermined driving distance of the driving element 160, namely, comparing the predetermined driving distance of the push rod 52 with the actual displacement magnitude of the push rod 52.

In the present embodiment, when the actual displacement magnitude of the push rod 52 is smaller than the driving distance predetermined by the driving element 160, the driving element 160 performs calibration according to a difference between the predetermined displacement distance of the push rod 52 and its actual displacement magnitude. Accordingly, through the feedback of the probing module 120, the driving element 160 can calibrate the driving distance of the push rod 52 more precisely and thereby mitigate the issue of excessive or insufficient injection amount injected by the syringe 50 resulting from the inability to precisely control the displacement of the push rod 52 of the syringe 50.

Referring back to FIG. 1, in the present embodiment, the peritoneal dialysis system 10 further includes a display element 16, and the display element 16 is disposed at a side of the housing 12 of the peritoneal dialysis system 10. The display element 16 is configured to display a sensing result of the displacement sensing device 100, e.g., the displacement distance of the push rod 52 of the syringe 50, a count of repetitive movements of the push rod 52, an amount of medicament injection of the syringe 50, etc.

In the present embodiment, the peritoneal dialysis system 10 further includes a fixing element 14, and the fixing element 14 is disposed between the guide rod 110 and the push rod 52 of the syringe 50. Moreover, the guide rod 110 and the push rod 52 respectively penetrate through and fixed to the fixing element 14 along their movement direction. As shown in FIG. 1 and FIG. 2, in the present embodiment, the fixing element 14 is connected to the driving element 160, and the driving element 160 drives the fixing element 14 to further move the guide rod 110 and the push rod 52 through the fixing element 14. In the present embodiment, through the configuration of the fixing element 14, the displacement sensing device 110 stabilizes the sliding movement of the guide rod 110 and the push rod 52 to prevent upward-downward or leftward-rightward skewness during the sliding movement.

Figure 3:
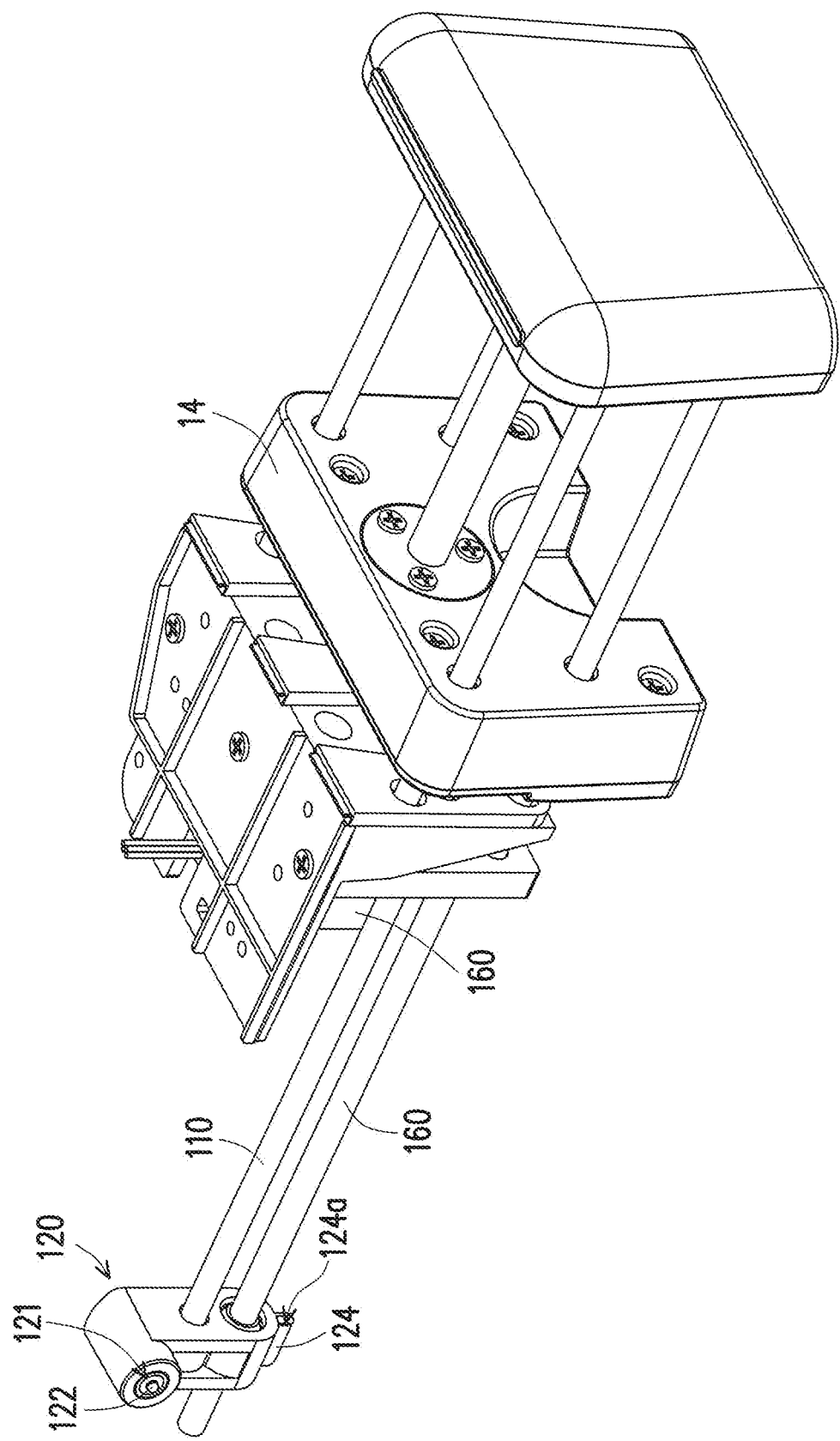
FIG. 3 is a schematic diagram illustrating part of components of the displacement sensing device of FIG. 2.

FIG. 3 is a schematic diagram illustrating part of components of the displacement sensing device of FIG. 2. Referring to FIG. 2 and FIG. 3, in the present embodiment, the displacement sensing device 100 further includes an optical sensor 150, disposed at the actuating initial position of the probing module 120 as shown in FIG. 2. Moreover, as shown in FIG. 3, the probing module 120 includes an extension part 124 and an optical shutter 124a, and the optical shutter 124a is disposed on the extension part 124. In the present embodiment, when the probing module 120 is located at the actuating initial position as shown in FIG. 2, a position of the optical shutter 124a of the probing module 120 is aligned with a position of the optical sensor 150. Specifically, the optical sensor 150 may be disposed at a side of the actuating initial position of the probing module 120, and through the optical shutter 124a, the optical sensor 150 may sense whether the probing module 120 returns to the original actuating initial position, so as to perform return-to-zero calibration on the probing module 120 with respect to its actuating initial position.

Figure 4:
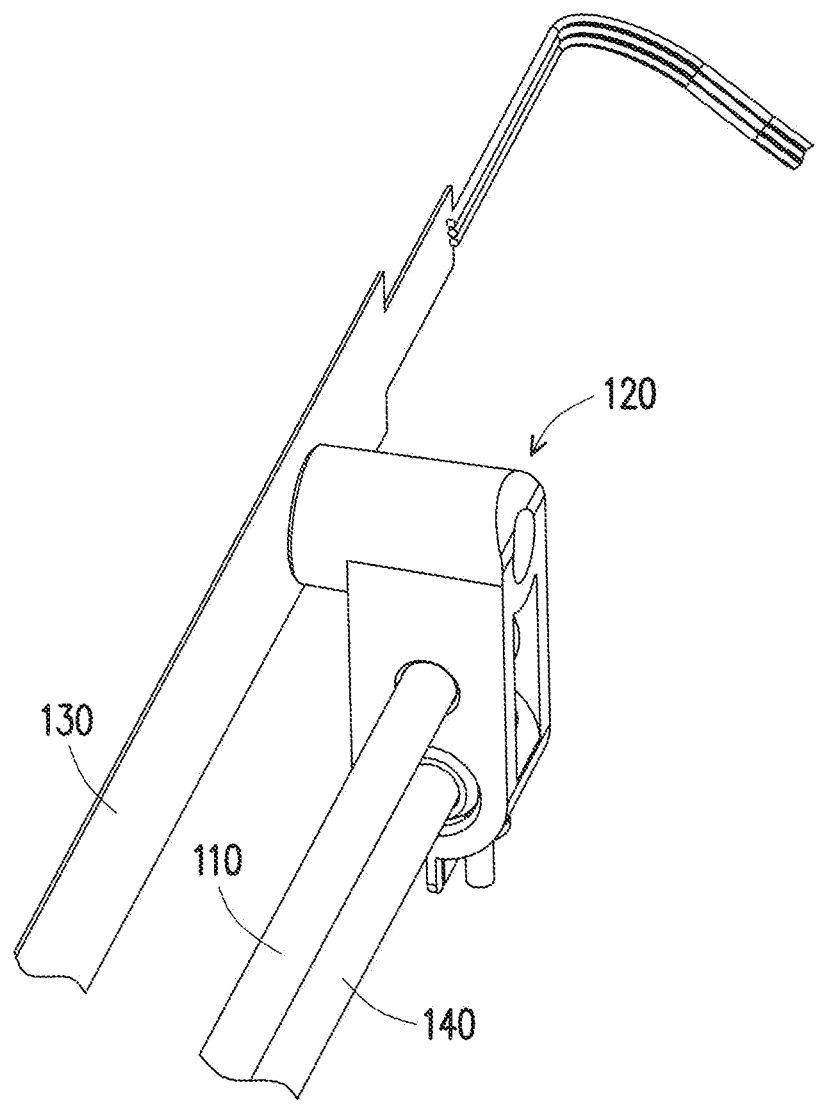
FIG. 4 is a schematic diagram illustrating part of components of the displacement sensing device of FIG. 2.

FIG. 4 is a schematic diagram illustrating part of components of the displacement sensing device of FIG. 2. Referring to FIG. 3 and FIG. 4, in the present embodiment, the probing module 120 further includes a threaded hole 121 and a probe 122, and the probe 122 may be locked by being screwed into the threaded hole 121 to contact the resistance scale 130. Specifically, in the present embodiment, a strength of the force by which the probe 122 of the probing module 120 contacts the resistance scale 130 may be controlled by a depth of the probe 122 locked into the threaded hole 121. For example, when a contact force is required between the probe 122 of the probing module 120 and the resistance scale 130, the depth of the probe 122 locked by being screwed into the threaded hole 121 may be reduced to increase a proportion of the probe 122 protruding from the threaded hole 121, such that the probe 122 can more tightly contact the resistance scale 130.

As shown in FIG. 3 and FIG. 4, the displacement sensing device 100 further includes a sliding rod 140, which has one end connected to the housing 12 and penetrates through the probing module 120. The probing module 120 slides relatively to the sliding rod 140. In the present embodiment, in the process where the probing module 120 is driven by the guide rod 110, the movement of the probing module 120 may be stabilized by the sliding rod 140 penetrating therethrough, so as to prevent the probing module 120 from shaking upwards and downwards in the process of being moved and contacting the resistance scale 130, which would impact on the measurement result.

In summary of the above, in the embodiments of the disclosure, the peritoneal dialysis system includes the displacement sensing device, and the displacement sensing device defines the displacement distance of the push rod of the syringe through the probing module and the resistance scale. Specifically, the probing module obtains the displacement distance of the guide rod and the push rod according to the measured resistance value on the resistance scale. Moreover, the driving element performs calibration according to the measurement result of the displacement of the push rod provided by the probing module. For example, if the displacement distance of the push rod provided by the probing module is smaller than the predetermined driving distance of the driving element, the driving element performs correction and control according to the difference between the displacement distance provided by the probing module and the predetermined displacement distance. Therefore, the displacement sensing device in the embodiments of the disclosure can prevent insufficient displacement of the push rod of the syringe in the driving process, which causes the amount of medicament actually drew or injected by the syringe to be less than the original predetermined injection amount. Accordingly, through the displacement sensing device, the peritoneal dialysis system can more precisely control the injection amount of medicament and a drawing amount of body fluids during the treatment and further reduce the occurrence of misdiagnosis in the treatment.

Although the disclosure is disclosed as the embodiments above, the embodiments are not meant to limit the disclosure. Any person skilled in the art may make slight modifications and variations without departing from the spirit and scope of the disclosure. Therefore, the protection scope of the disclosure shall be defined by the claims attached below.

What is claimed is:

1. A displacement sensing device, configured for a peritoneal dialysis system comprising a housing and a syringe disposed on the housing and having a push rod, the displacement sensing device comprising:

a guide rod coupled to the push rod;
a probing module disposed in the housing and fixed at the guide rod;
a resistance scale disposed at a side of the probing module, wherein the guide rod is configured to drive the probing module and the push rod to move towards the same direction, and the probing module is configured to contact the resistance scale to obtain a resistance value of the resistance scale and determine a displacement magnitude of the push rod; and
a sliding rod connected to the housing and penetrating through the probing module, wherein the probing module is configured to slide relatively to the sliding rod.

2. The displacement sensing device according to claim 1, further comprising a driving element coupled to the guide rod and the push rod to drive the guide rod and the push rod to move.

3. The displacement sensing device according to claim 2, wherein the driving element comprises a stepping motor.

4. The displacement sensing device according to claim 1, further comprising an optical sensor disposed at an actuating initial position of the probing module to perform return-to-zero calibration for traveling displacement of the probing module.

5. The displacement sensing device according to claim 4, wherein the probing module comprises an extension part, and the extension part comprises an optical shutter corresponding to the optical sensor.

6. The displacement sensing device according to claim 1, wherein the probing module further comprises a threaded hole and a probe, and the probe is locked by screwed into the threaded hole to contact the resistance scale.

7. A peritoneal dialysis system comprising:

a housing;
a syringe disposed on the housing, the syringe having a push rod; and
a displacement sensing device disposed in the housing, comprising:
a guide rod coupled to the push rod;
a probing module fixed at the guide rod;
a resistance scale disposed at a side of the probing module, wherein the guide rod is configured to drive the probing module and the push rod to move towards the same direction, and the probing module is configured to contact the resistance scale to read a resistance value of the resistance scale and determine a displacement magnitude of the push rod; and
a sliding rod connected to the housing and penetrating through the probing module, wherein the probing module is configured to slide relatively to the sliding rod.

8. The peritoneal dialysis system according to claim 7, further comprising a display element disposed at a side of the housing to display a sensing result of the displacement sensing device.

9. The peritoneal dialysis system according to claim 7, further comprising a fixing element disposed between the guide rod and the push rod, the guide rod and the push rod respectively penetrating through the fixing element along the same direction.

* * * * *